United States Patent
Makihara

[11] Patent Number: 5,365,029
[45] Date of Patent: Nov. 15, 1994

[54] DEVICE FOR DISPOSING INJECTION NEEDLES

[75] Inventor: Shinsaku Makihara, Yokohama, Japan

[73] Assignee: Esu Makku Co., Ltd., Kawasaki, Japan

[21] Appl. No.: 160,811

[22] Filed: Dec. 3, 1993

[30] Foreign Application Priority Data

Jul. 15, 1993 [JP] Japan .................... 5-197995

[51] Int. Cl.[5] ............... B23K 9/013; A61G 12/00; A61L 11/00
[52] U.S. Cl. .................................. 219/68
[58] Field of Search ............ 219/68; 110/250, 346

[56] References Cited

U.S. PATENT DOCUMENTS

| | | | |
|---|---|---|---|
| 4,447,694 | 5/1984 | Brochier et al. | 219/68 |
| 4,628,169 | 12/1986 | Ching-Lung | 219/68 |
| 4,961,541 | 10/1990 | Hashimoto | 219/68 |
| 4,965,426 | 10/1990 | Colombo | 219/68 |

FOREIGN PATENT DOCUMENTS

2-52652  2/1990  Japan .

*Primary Examiner*—Geoffrey S. Evans
*Attorney, Agent, or Firm*—Wenderoth, Lind & Ponack

[57] ABSTRACT

An injection syringe slot 28 for holding a tip of a syringe 30 detachably is formed on a case 2. A pair of shafts 4 and 6 connected to a rotary drive device is journalled on the case 2, and a plurality of elongate electrodes 8 and 10 are fixed to each of the shafts 4 and 6 at a predetermined interval. Each electrode 8 of the shaft 4 of one side forms a pair with each electrode 10 of the shaft 6 of the other side which is opposed to each other with a difference in level in axial direction, and a plurality of sets of a pair of electrodes are set so that the opposite interval of a pair of electrodes of a lower level is narrower than the opposite interval of a pair of electrodes in upper level. When the syringe 30 is inserted and set at the syringe slot 28 of the case, the syringe 30 is supported at the syringe slot. When the shafts 4 and 6 are driven, the electrode 8 of plus side and the electrode 10 of minus side approach to each side of an injection needle 42. Those approaching the needle 42 are a pair of electrodes 8 and 10 of the lowest level among the electrodes 8 and 10 opposed to both sides of the needle 42.

3 Claims, 7 Drawing Sheets

DEVICE FOR DISPOSING INJECTION NEEDLES

PRIOR ART

Many applications have been filed for devices for disposing injection needles by means of discharge, heat melting and the like and they become already prior arts.

In the official gazette of U.S. Pat. No. 5,138,124, a device for destructing used injection needles is disclosed in which an injection syringe is retained by hand, and a tip of the injection needle is urged against one of two rotating electrodes, and the injection needle melts by means of sparks.

Also, in the official gazette of U.S. Pat. No. 4,628,169, a structure of a device for destructing injection needles is disclosed in which an injection needle of an injection syringe is inserted into an elongate injection syringe slot while holding the injection syringe by hand, and the injection syringe is caused to slide along a longitudinal direction of the injection syringe slot while holding the injection syringe by hand, and the injection needle melts at its tip by sparks flying up between the electrodes.

Also, in the official gazette of Japanese Patent Laid-open No. 2-52652, a device for disposing injection needles is disclosed in which a plurality of electrodes are simultaneously caused to make contact with the injection needle, and voltage of a predetermined level is applied to the injection needle through the plurality of electrodes, and a temperature of the injection needle is elevated by a resistance heat up to cut off the injection needle at an optional number of locations of the injection needle.

SUMMARY OF THE INVENTION

The present invention relates to a device for disposing injection needles in which used injection needles for medical treatment melt by means of sparks.

Each of the devices disclosed in the above-noted official gazettes of the U.S. Pat. No. 5,138,124 and 4,628,169 required an attachment of the injection needle to the electrodes during the melting of the injection needle tip while an operator held the injection syringe by hand.

For this reason, the injection needle disposing operation was not easy, and moreover, the vibration of the sparks at the tip of the injection needle was transmitted to the hand which gave uncomfortable feeling on the part of the operator.

Also, a device of Japanese Patent Laid-open No. 2-52652 for cutting the injection needle with heat melting while the plurality of electrodes were simultaneously in contact with the injection needle required a structure of causing the plurality of electrodes to make contact with the injection needle simultaneously, and its structure became complicated.

Furthermore, a system of causing the plurality of electrodes simultaneously to abut on the injection needle caused a problem of producing the uncertainty about which of the electrodes caused the cutoff of the injection needle, and in some cases, the cutoff occurred initially at the root of the injection needle. When the cutoff portion dropped, the injection needle was not cut into small pieces.

An object of this invention is to provide a device for disposing injection needles in which an operation of melting and cutting of the injection needle may be carried out by free hand, namely, even if the operator leaves his hand off the injection syringe, after the syringe is set at an injection syringe slot, and the injection needle may be cut into small pieces from the tip toward the root in sequence.

The present invention is constructed in such a way that a pair of shafts connected to a rotary drive device is journalled on a case, and a plurality of elongate electrodes are fixed on each of the shafts in a horizontal direction at a predetermined interval. Each electrode of one shaft constitutes an electrode at plus side, and each electrode of the other shaft at minus side which is opposed to them forms a pair respectively, and a difference in level is provided for height so that the electrode at one shaft side and the electrode at the other shaft are mutually crossed without causing the collision when they approach to each other.

An opposite interval between the electrode at one shaft side forming a pair with the electrode at the other shaft side is set to be narrower for the opposite interval of a pair of electrodes of lower level against the opposite interval of a pair of electrodes of higher level, and with this arrangement, the opposite interval between the electrode of one shaft forming a pair with the electrode of the other shaft is arranged to be narrower in sequence towards the lower part of the injection needle disposed at the center of each pair of electrodes.

The used syringe is set at the syringe slot of the case, and the injection needles of the syringe is disposed almost at a center of an opposite space portion of the electrode group at one side and the electrode group of the other side.

When a pair of shafts is rotated in mutually opposite directions from a return position by means of a solenoid, a pair of electrodes of the lowest level touches the lower part of the injection needle, and the other electrode of the upper level is engaged at a position which is separated from the injection needle.

When the pair of electrodes of the lowest level makes contact with the injection needle, the electrodes are shortcircuited, which produces a spark phenomenon, and the portion of the injection needle which is in contact with the pair of electrodes melts and cut off.

When the injection needle is cut off, the pair of electrodes of upper level makes contact with the injection needle. When this operation is carried out in sequence, the injection needle is cut into small pieces in sequence from the tip to the root with each predetermined portion being directed upward.

DETAILED DESCRIPTION OF THE PREFERRED EMBODIMENTS

A structure of the present invention will be described in the following in detail by referring to embodiments illustrated in attached drawings.

Reference numeral 2 denotes a case, and numerals 4 and 6 denote shafts rotatably supported on a top and bottom wall of the case 2 by means of a ball bearing, and they are mutually in parallel at a predetermined interval. Each of a plurality of electrodes 8 and 10 consisting of elongate plate-like small pieces is fixed to the shafts 4 and 6 at a fixed interval.

Figure 6:
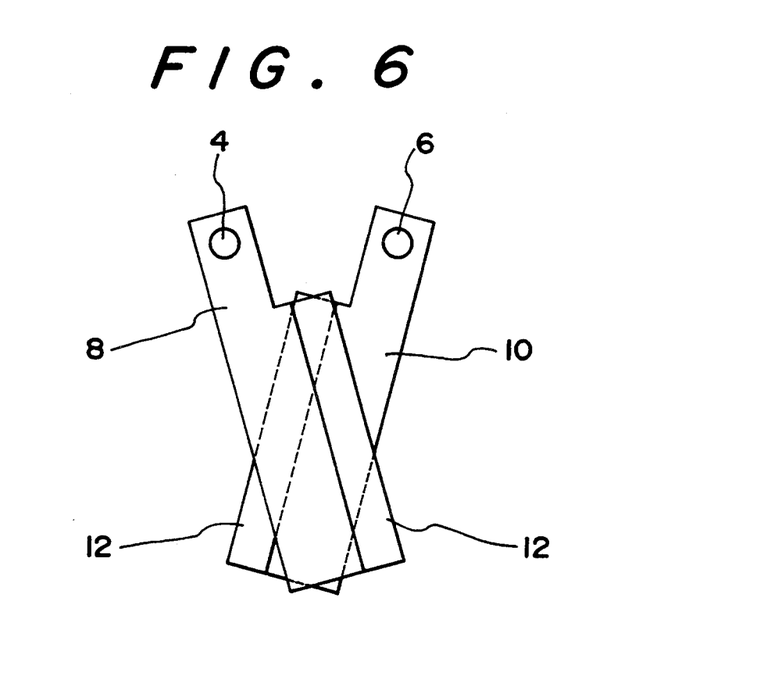
FIG. 6 is a plan view showing a condition where an electrode of one side forming a pair with an electrode of the other side is crossed with the other.

A difference in level is formed in height of the electrode 8 at the shaft 45 side and in height of the electrode 10 at the shaft 6 side, and the corresponding pair of electrodes 8 and 10 is arranged to be crossed as shown in FIG. 6 when they approach to each other.

An opposite interval of each electrode 8 and that of each electrode 10 along the shafts 4 and 6 are set slightly wider than a thickness of the electrode.

Five pieces of the electrodes 8 at the shaft 4 side are provided in this embodiment, and identical five pieces of the electrodes 10 at the other shaft 6 side are provided.

The electrodes 8 are directed to an identical direction respectively, and also, the electrodes 10 are directed to an identical direction, and each of them is fixed to the shafts 4 and 6.

A belt like silicon carbide 12 or a beltlike sintered graphite is fixed to opposite sides of the electrodes 8 of the shaft 4 side and that of the electrode 10 of the shaft 6 side.

The electrodes 8 and 10 are of such that a width L of each is set at a wider value for the lower level electrodes, and a pair of the electrode 8 of one side and the electrode 10 of the other side has the same width L.

Figure 5:
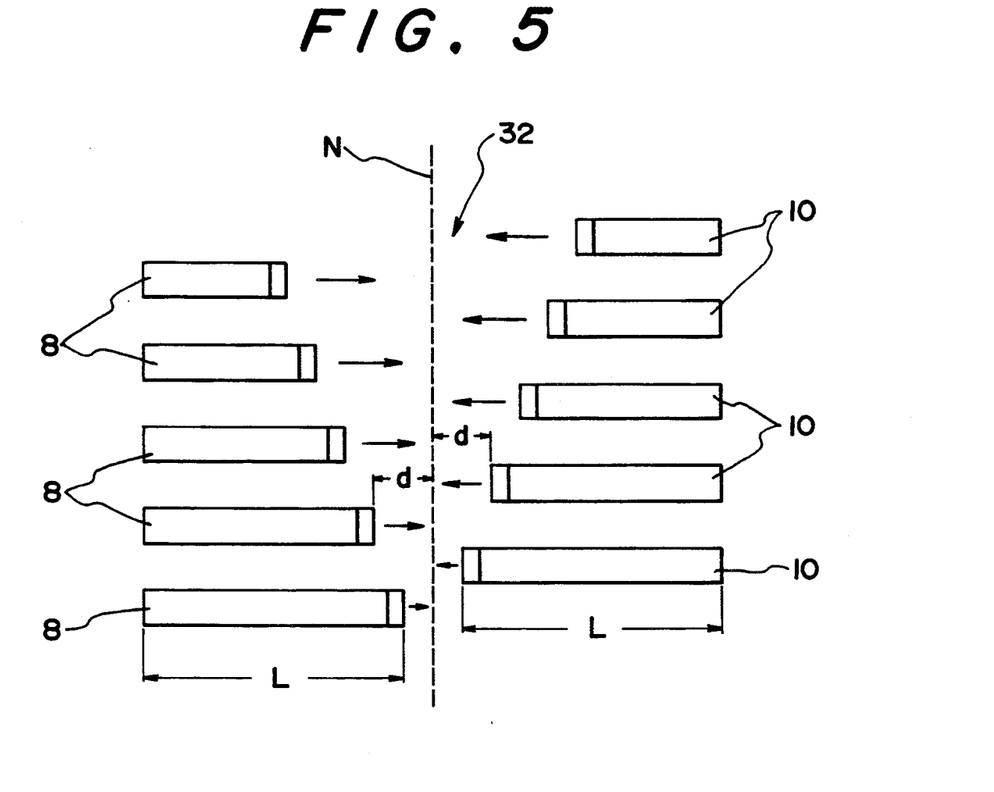
FIG. 5 is an drawing for explanation of an operation of electrodes.

A pair of the electrodes 8 and 10 as shown in FIG. 5, is opposed at an equal interval d against a center axis N of the opposite space portion S between the electrode 8 group of one side and the electrode 10 group of the other side.

An opposite interval D based on the center axis N as a standard of a pair of the electrodes 8 and 10 is set at a narrower value for the lower level than the upper level. Namely, the interval d becomes smaller as the electrodes positioned at lower levels.

Accordingly, when the shafts 4 and 6 are rotated in mutually counter directions, and the electrode 8 group of the shaft 4 side and the electrode 10 group of the shaft 6 side approach to each other, a pair of the lower electrodes 8 and 10 is piled on each other in the first place, and then, the pair of the electrodes 8 and 10 which are of next upper level are piled upon another, and the superposed conditions are arranged to shift upwards in sequence according to the rotation of the shafts 4 and 6.

Figure 3:
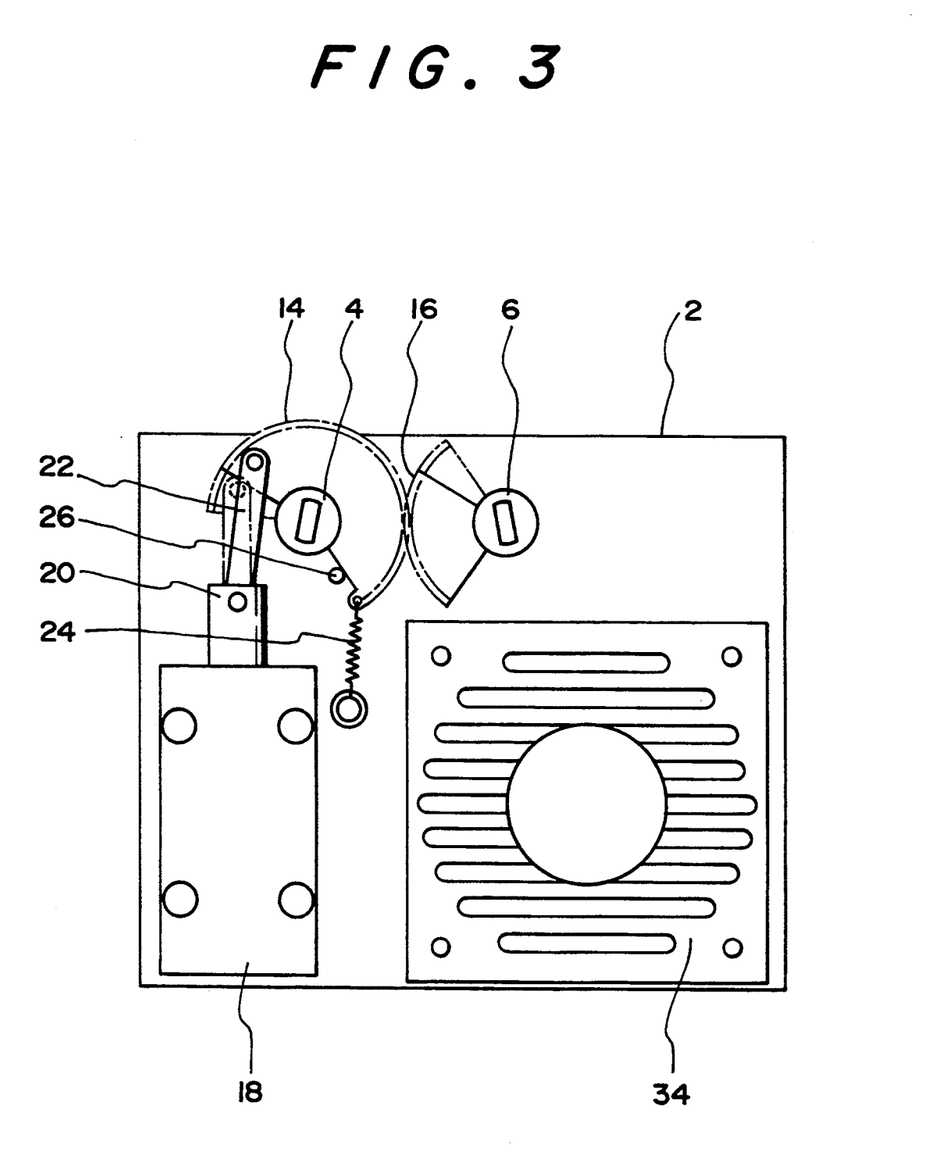
FIG. 3 is a bottom view of a case showing a rotary drive means of shafts.

As shown in FIG. 3, fan-shaped gears 14 and 16 are fixed to lower portions of the shafts 4 and 6, and they are mutually meshed.

Numeral 18 denotes a solenoid fixed to a lower wall of the case 2, and one end of a connecting link plate 22 is rotatably journalled on an output shaft 20 of the solenoid and the other end of the connecting link plate 22 is rotatably journalled to an eccentric portion of the fan-shaped gear 14.

The fan-shaped gear 14 is energized in a clockwise direction in FIG. 3 by means of a tensile force of a return coil spring 24, and a side surface of the fan-shaped gear 14 is resiliently engaged with a stopper shaft 26 by the energizing force which is projected on a bottom surface of the case 2.

Numeral 28 denotes an injection syringe slot, and is composed of a tapered guide portion 28a that opens to an upper surface of the case 2 and a taper tube like holding portion 28b for fitting and holding a tip portion 30a of an injection syringe 30 detachably.

The syringe slot 28 is disposed at a center axis N in the middle of an opposite space portion 32 formed by opposing one electrode 8 and the other electrode 10.

Numeral 34 denotes a blower fixed to the bottom of the case 2, and its blowing opening is opposed to a plurality of through holes (not shown in the drawing) perforated on the lower wall of the case 2.

Figure 8:
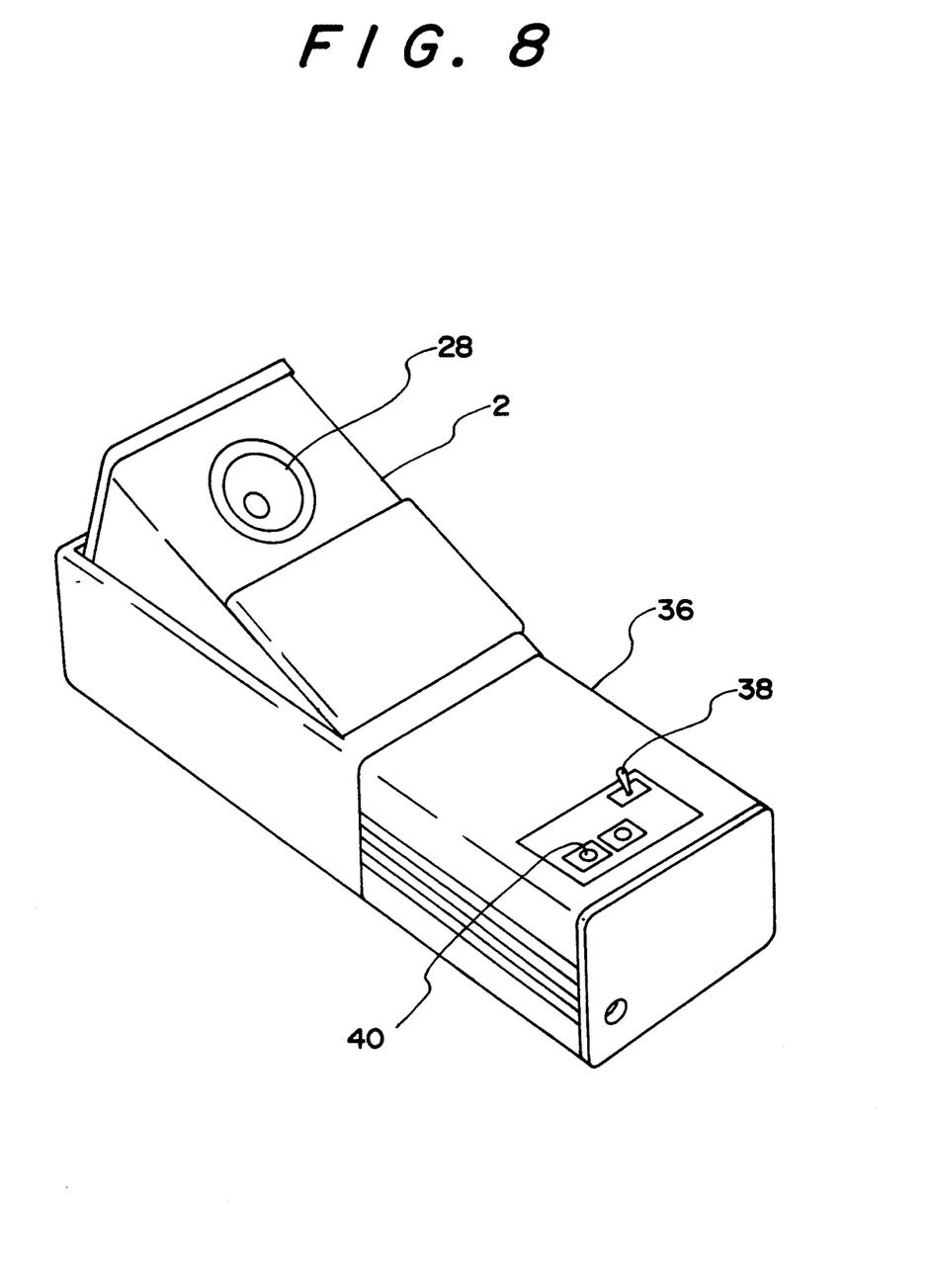
FIG. 8 is a general view of this invention.

The case 2 is mounted on a cabinet 36 aslantly as shown in FIG. 8.

The electrodes 8 and 10 are electrically connected to shafts 4, 6 and a power source switch provided on an operation panel of the cabinet 36 and a battery (not shown in the drawing) in the cabinet 36 by means of a boosting circuit, and each electrode 8 at the shaft 6 side is impressed with plus voltage and each electrode 10 at the shaft 6 side is impressed with minus voltage.

The solenoid 18 is connected to the battery by means of a solenoid control circuit (not shown in the drawing) built in the cabinet 36, and when an operation push button switch 40 is pressed down, a solenoid drive current pulse of a predetermined pulse width is supplied to the solenoid 18 at a predetermined period, and when hand leaves the switch 40, the supply of the solenoid drive current pulse is stopped.

An operation of the present embodiment will be described in the following.

When the tip portion 30a of the syringe 30 provided with a needle 42 is inserted into the syringe slot 28, the tip portion 30a is retained at the holding portion 28b of the syringe slot 28.

In a normal condition, the fan-shaped gear 14 is engaged with the stopper shaft 26 by the tensile force of the spring 24, and the electrode 8 group of the shaft 4 side and the electrode 10 group of the shaft 6 side are opposed at a predetermined interval.

The needle 42 of the syringe 30 retained at the syringe slot 28 is positioned at a middle of the opposite space portion 32 of the electrode 8 group and the electrode 10 group.

Figure 1:
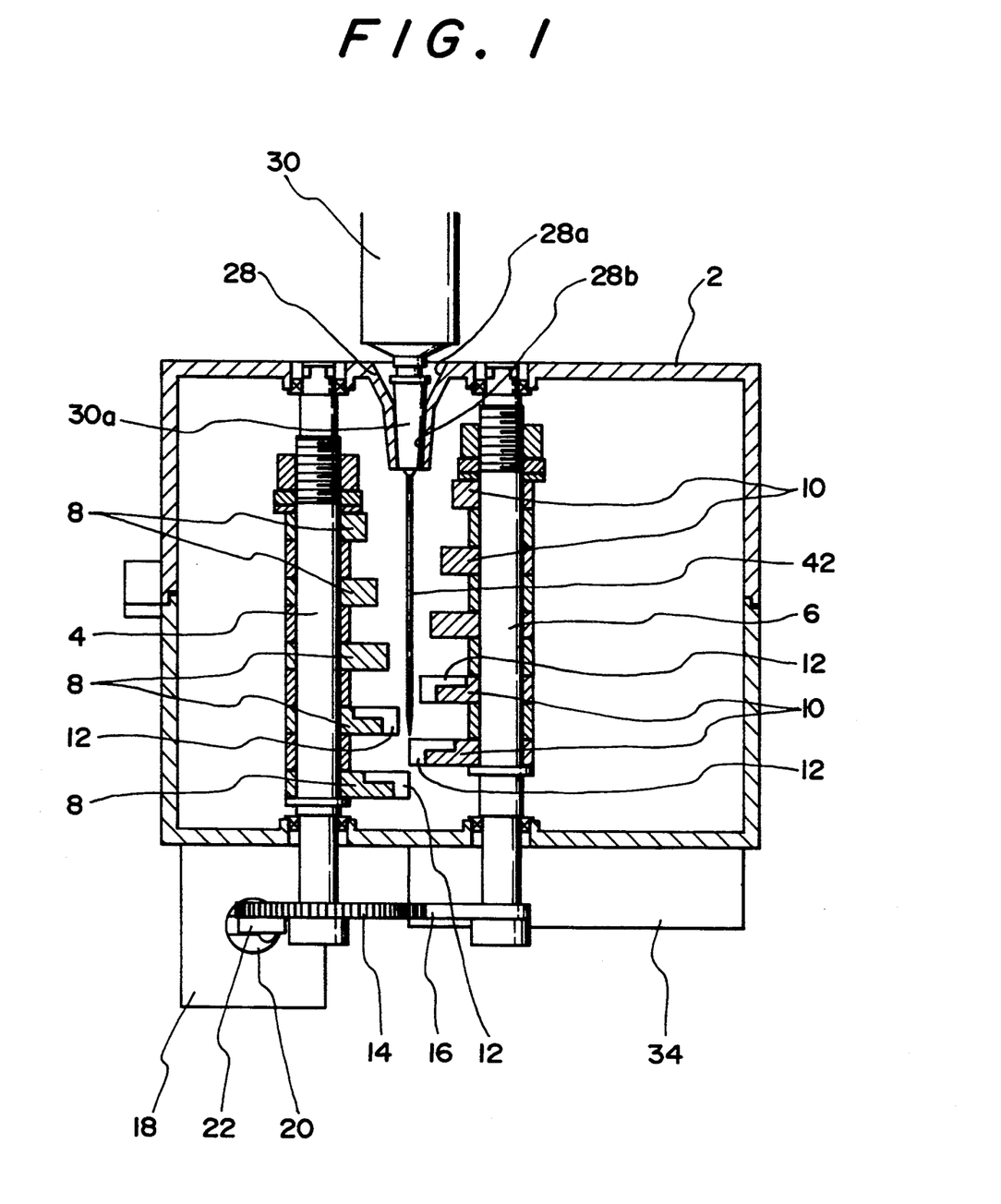
FIG. 1 is a cross sectional view showing an internal structure of a case.
Figure 2:
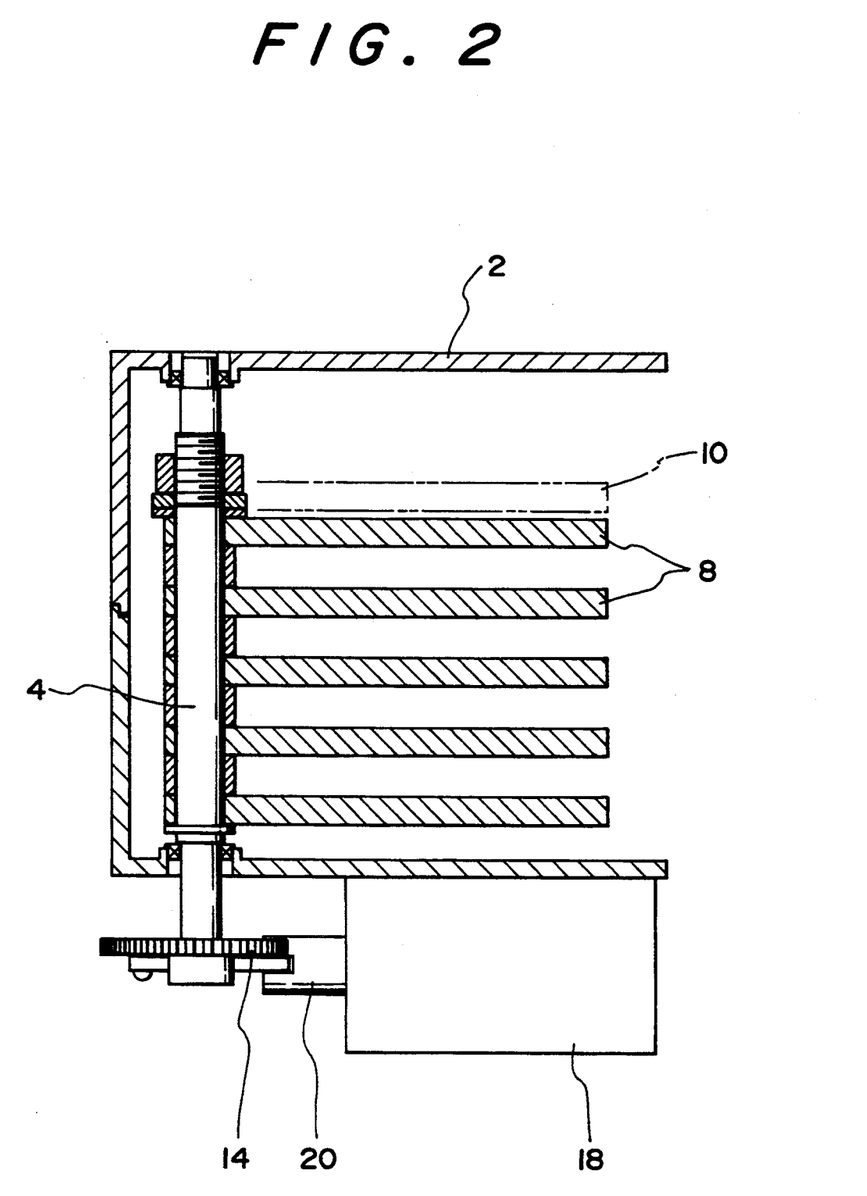
FIG. 2 is a cross sectional view showing a mounting structure of electrodes.

In the entire region from the tip to the root of the needle 42 of a standard dimension, as shown in FIG. 1, four sets of a pair of electrodes 8 and 10 are opposed. By the way, a pair of electrodes 8 and 10 which is positioned at the lower part of the tip of the needle 42 and not being in contact with the tip thereof is for the longer needles, and this pair of electrodes crosses with each other as shown in FIG. 6.

When an operator turns the power source switch 38 on, and the operation switch 40 is pressed down, pulse current is supplied to the solenoid 18.

This pulse current has a predetermined pulse width, and while the operation switch is pressed down, it is supplied to the solenoid 18 repeatedly at a predetermined period.

When the solenoid 18 is energized, the output shaft 20 is attracted by the electromagnetic force, and the fan-shaped gear 14 is rotated in counterclockwise direction in FIG. 3, and accordingly, the fan-shaped gear 16 is rotated in counterclockwise direction.

Figure 4:
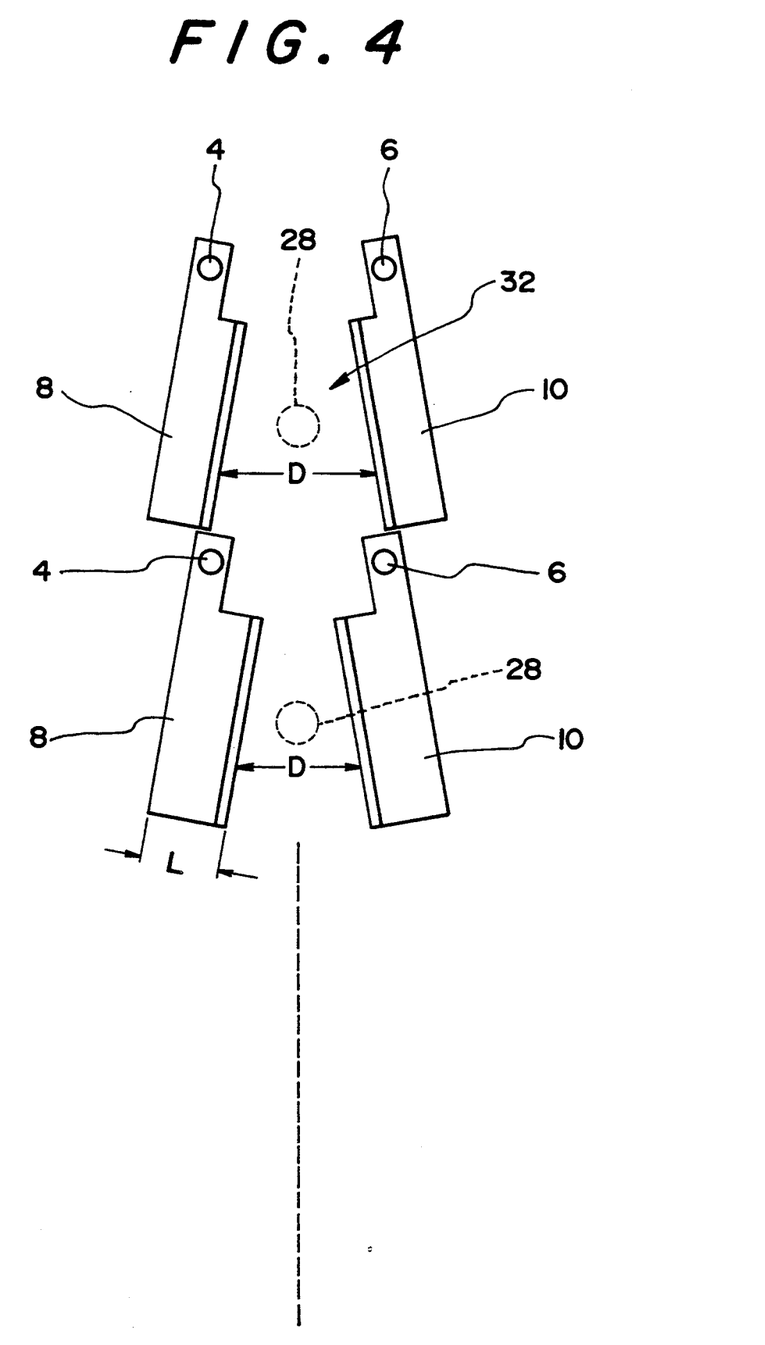
FIG. 4 is a drawing for explanation of a disposed condition of electrodes.

The shafts 4 and 6 are rotated by the rotation of the fan-shaped gears 14 and 16, and the electrode 8 group of one part and the electrode 10 group of the other part are oscillated in a direction where the electrode groups mutually cross (refer to FIG. 6) in the opposite condition (refer to FIG. 4) at a predetermined interval.

Figure 7A:
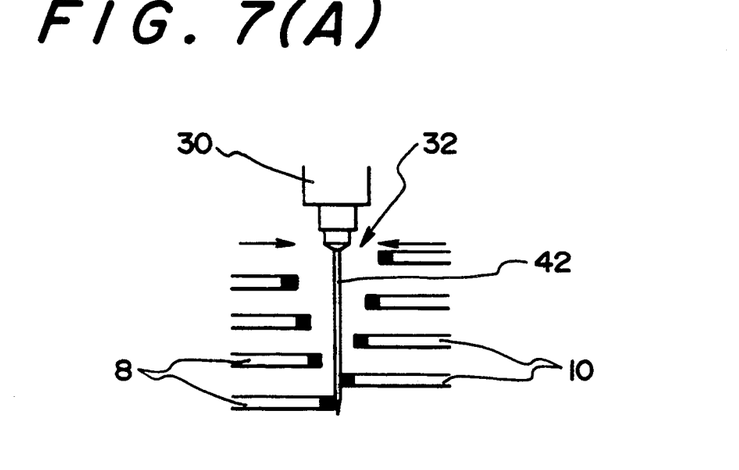
FIGS. 7(A), 7(B), and 7(C) are drawings for explanation of an operation of this invention.

At this time, a pair of electrodes 8 and 10 which is of the lowest level and being opposed to the needle 42 makes contact with the lower portion of the needle 42 as shown in FIG. 7A.

Figure 7B:
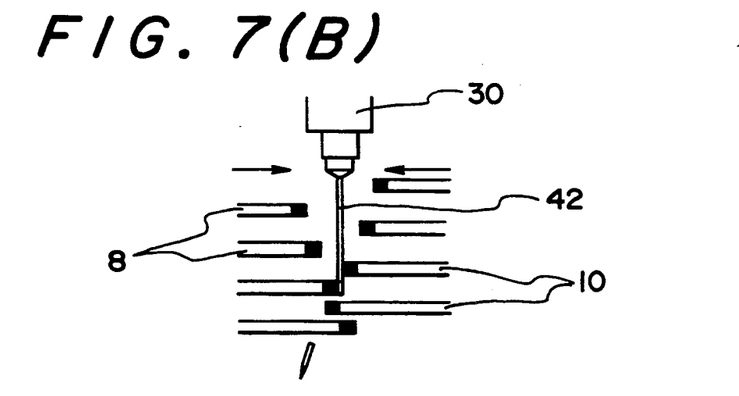
Figure 7C:
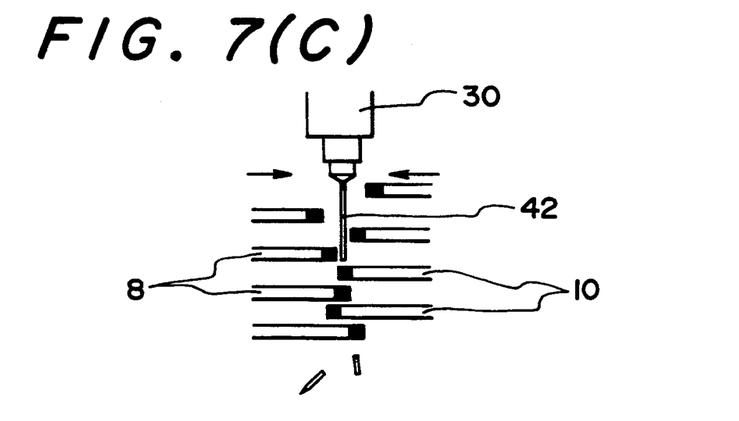

The foregoing contact causes a short circuit (short) between a pair of electrodes 8 and 10 to flow a shortcircuit current between the electrodes 8 and 10, causing sparks, and the portion of the needle contacting with the pair of electrodes 8 and 10 melts and cut off. When the needle 42 disposed between the pair of electrodes 8 and 10 melts and cut off, this pair of electrodes 8 and 10 loses the support, and is subjected to the oscillation in mutually crossing directions by the drive force of the output shaft 20 of the solenoid 18, and a pair of electrodes 8 and 10 of an upper level makes contact with the needle 42 by the oscillation as shown in FIG. 7B.

The portion of the needle 42 contacting the pair of electrodes 8 and 10 melts by the sparks between the pair of electrodes 8 and 10 by the contact.

As described in the foregoing, each of a pair of electrodes 8 of the shaft 4 side and electrode 10 of the shaft 6 side makes contact with the needle 42 at a time by moving from the lower part to the upper part of the needle 42, and the needle 42 melts, and is cut into pieces from the lower part to the upper part, and drops downward.

At this time, the needle itself is heated up to a high temperature (a temperature at which stainless steel melts is about 1500 centigrade) whereby disinfection and sterilization are achieved.

When the energization to the solenoid 18 is turned off, the shafts 4 and 6 are rotated in a return direction by the tensile force of the spring 24, and the electrode 8 group and the electrode 10 group are separated from each other at a predetermined interval.

The foregoing operation repeatedly goes on while the operation switch 40 is pressed down, and the needle 42 is cut into small pieces, and the needle 42 is subjected to heat treatment.

The present invention has been constructed as described in the foregoing, and there is an effect that a melting operation of the needle may be performed in a free hand manner after making an insertion of the syringe into the syringe slot of the case, and moreover, the sparks fly up from the lower part of the syringe in sequence toward the upper part thereof to allow the melting and cutting of the needle into small pieces effectively.

What is claimed is:

1. In a device for disposing injection needles in which an injection needle is sandwiched between an electrode of one side and an electrode of the other side, and sparks fly up between the electrodes to melt the needle, the improvement comprising:
    a case 2;
    a pair of shafts 4 and 6 which is rotatably journalled on the case 2 which are mutually in parallel;
    a rotary drive means for synchronously driving said pair of shafts 4 and 6 by a predetermined torque in mutually counter directions;
    a plurality of elongate electrodes 8 of one side fixed to the shaft 4 of the pair of shafts 4 and 6 at a predetermined interval mutually and projecting at right angles to the shaft 4;
    a plurality of elongate electrodes 10 of the other side fixed to the shaft 6 of the pair of shafts 4 and 6 at a predetermined interval mutually and projecting at right angles to the shaft 6 and forming a plurality of sets of pairs with each of the electrodes of one side disposed in opposition with a difference in level with the electrodes 8 of the one side so that it crosses with the electrode 8 of one side;
    a means for impressing voltage for flying up sparks between the electrodes 8 of one side and the electrodes 10 of the other side; and
    an injection syringe slot 28 having a holding portion 28b that holds a tip portion of the syringe detachably which is positioned on an extension of an axis at an almost center of an opposite space portion between the electrodes 8 of one side and the electrodes 10 of the other side and being provided on the case 2, whereby an opposite interval D between each pair of opposite side surface of the electrodes 8 of one side and that of the electrodes 10 of the other side is narrowed in sequence toward a direction of a lower end of the needle 42 disposed at a center of the opposite space portion formed by the electrodes 8 and 10.

2. The device for disposing injection needles according to claim 1 in which silicon carbide 12 is fixed to a side surface of at least one surface of the electrodes 8 of one side and a side surface of at least one surface of electrodes 10 of the other side, for making contact at the needle 42.

3. The device for disposing injection needles according to claim 1 in which sintered graphite is fixed to a side surface of at least one surface of the electrodes 8 of one side and a side surface of at least one surface of electrodes 10 of the other side, for making contact at the needle 42.

* * * * *